United States Patent
Shiramizu et al.

(10) Patent No.: US 12,077,482 B2
(45) Date of Patent: Sep. 3, 2024

(54) AMPHIPHILIC REACTION PRODUCTS FROM VINYLIDENE OLEFINS AND METHODS FOR PRODUCTION THEREOF

(71) Applicant: ExxonMobil Chemical Patents Inc., Baytown, TX (US)

(72) Inventors: Mika L. Shiramizu, Houston, TX (US); Alan A. Galuska, Ellijay, GA (US); Alex E. Carpenter, Seabrook, TX (US); Jennifer L. Rapp, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 203 days.

(21) Appl. No.: 17/615,638

(22) PCT Filed: May 14, 2020

(86) PCT No.: PCT/US2020/032822
§ 371 (c)(1),
(2) Date: Dec. 1, 2021

(87) PCT Pub. No.: WO2020/256862
PCT Pub. Date: Dec. 24, 2020

(65) Prior Publication Data
US 2022/0306556 A1 Sep. 29, 2022

Related U.S. Application Data

(60) Provisional application No. 62/864,289, filed on Jun. 20, 2019.

(30) Foreign Application Priority Data

Aug. 28, 2019 (EP) .................................... 19194191

(51) Int. Cl.
C07C 15/00 (2006.01)
C07C 15/107 (2006.01)
(Continued)

(52) U.S. Cl.
CPC .......... C07C 15/107 (2013.01); C07C 309/31 (2013.01); C11D 1/04 (2013.01);
(Continued)

(58) Field of Classification Search
None
See application file for complete search history.

(56) References Cited

U.S. PATENT DOCUMENTS

| | | | |
|---|---|---|---|
| 4,954,325 A | 9/1990 | Shiramizu | 423/328 |
| 5,334,795 A | 8/1994 | Chu et al. | 585/467 |

(Continued)

FOREIGN PATENT DOCUMENTS

| | | | | |
|---|---|---|---|---|
| WO | WO1997/000843 | 1/1997 | | C07C 43/11 |
| WO | WO2020/131286 | 6/2020 | | C07C 303/06 |

OTHER PUBLICATIONS

Varadaraj, R. et al. (1991) "Fundamental interfacial properties of alkyl-branched sulfate and ethoxy sulfate surfactants derived from Guerbet alcohols. 1. Surface and instantaneous interfacial tensions," *J. Phys. Chem.*, v.95(4), pp. 1671-1676.

*Primary Examiner* — Necholus Ogden, Jr.

(57) ABSTRACT

Compositions comprising one or more amphiphilic compounds formed from vinylidene olefins may comprise: a reaction product of one or more vinylidene olefins, in which the reaction product comprises a hydrophobic portion and a hydrophilic portion comprising a polar head group bonded to the hydrophobic portion. The one or more vinylidene olefins each comprise a vinylidene group that undergoes a reaction to become saturated and to produce at least part of the hydrophobic portion.

3 Claims, 4 Drawing Sheets

(51) Int. Cl.
  *C07C 309/31*  (2006.01)
  *C11D 1/04*  (2006.01)
  *C11D 1/12*  (2006.01)
  *C11D 1/29*  (2006.01)
  *C11D 1/66*  (2006.01)

(52) U.S. Cl.
  CPC .................. *C11D 1/12* (2013.01); *C11D 1/29* (2013.01); *C11D 1/66* (2013.01); *C11D 1/667* (2013.01)

(56) References Cited

U.S. PATENT DOCUMENTS

| | | | |
|---|---|---|---|
| 5,674,950 | A | 10/1997 | Thaler et al. ............... 525/337.1 |
| 6,566,319 | B1 | 5/2003 | Scheibel et al. ............... 510/357 |
| 10,604,462 | B2 | 3/2020 | Chen et al. ........... C07C 29/141 |
| 10,654,766 | B2 | 5/2020 | Chen et al. ................ C07C 2/34 |
| 2006/0052630 | A1 | 3/2006 | Narbeshuber et al. ......... 562/81 |
| 2008/0234157 | A1 | 9/2008 | Shiramizu ..................... 508/591 |
| 2017/0369816 | A1 | 12/2017 | Holland et al. .......... C11D 1/37 |
| 2018/0282359 | A1 | 10/2018 | Crowther et al. ...... C07F 17/00 |

AMPHIPHILIC REACTION PRODUCTS FROM VINYLIDENE OLEFINS AND METHODS FOR PRODUCTION THEREOF

CLAIM TO PRIORITY

This application is a national stage filing of Patent Cooperation Treaty Application No. PCT/US2020/032822 filed May 14, 2020 claiming priority to U.S. Provisional Application No. 62/864,289, filed Jun. 20, 2019, and European Patent Application No. 19194191.3, filed Aug. 28, 2019, the disclosures of the U.S. Provisional Application and the European Patent Application are incorporated herein by reference.

BACKGROUND

Surfactants are compounds that tend to lower the surface tension at an interface between two components. As such, surfactants may be used in a wide range of applications, which may include, for example, promoting solubility of an otherwise sparingly soluble solid, lowering viscosity of a fluid phase, and promoting foaming of a fluid. Surfactants may be found in a wide range of consumer and industrial products including, for example, soaps, detergents, cosmetics, pharmaceuticals, and dispersants.

Surfactants feature both hydrophobic and hydrophilic portions within their molecular structure. As such, surfactants are amphiphilic. Hydrophobic portions are generally non-ionic and may include saturated or unsaturated hydrocarbyl groups, such as alkyl, alkenyl, or aryl groups. Hydrophilic portions, in contrast, feature polar head groups that may be ionic, non-ionic, or zwitterionic and encompass a range of polar functional groups or moieties. Ionic functional groups that may be present in the hydrophilic portion of surfactants include, for example, sulfonates, sulfates, carboxylates, phosphates, quaternary ammonium groups, and the like. Non-ionic hydrophilic portions may include functional groups or moieties bearing one or more heteroatoms that are capable of receiving hydrogen bonds, such as polyethers (e.g., ethoxylates). Zwitterionic hydrophilic portions may include moieties such as betaines, sultaines, and related phospholipid compounds.

Surfactants finding extensive commercial use generally feature a relatively limited range of structure types. Common classes of commercial surfactants include, for example, alkylbenzene sulfonates, lignin sulfonates, long chain fatty alcohol sulfates, long chain fatty acid carboxylates, long chain fatty alcohol ethoxylates, long chain quaternary ammonium compounds, and alkylphenol ethoxylates. The various classes of surfactants may exhibit a range of surfactant properties, and there may be further property variation within the members or homologues within each class. Accordingly, a surfactant for a given application may be chosen based upon various application-specific requirements. There remains a need, however, for development of additional types of surfactants having additional structural diversity to accommodate presently unmet or unknown application-specific requirements within various industries.

References of interest include DE 102 61 481 A1; U.S. Pat. No. 6,566,319; WO 1997/00843; and US 2017/369816 A1.

SUMMARY

Compositions described herein may comprise a reaction product of one or more vinylidene olefins, the reaction product comprising a hydrophobic portion and a hydrophilic portion comprising a polar head group bonded to the hydrophobic portion. The one or more vinylidene olefins each comprise a vinylidene group that undergoes a reaction to become saturated and to produce at least part of the hydrophobic portion.

Detergent formulations described herein may comprise an aqueous fluid and a surfactant comprising a reaction product of one or more vinylidene olefins at a concentration is ranging from 10 wt % to 80 wt % in the aqueous fluid.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1:
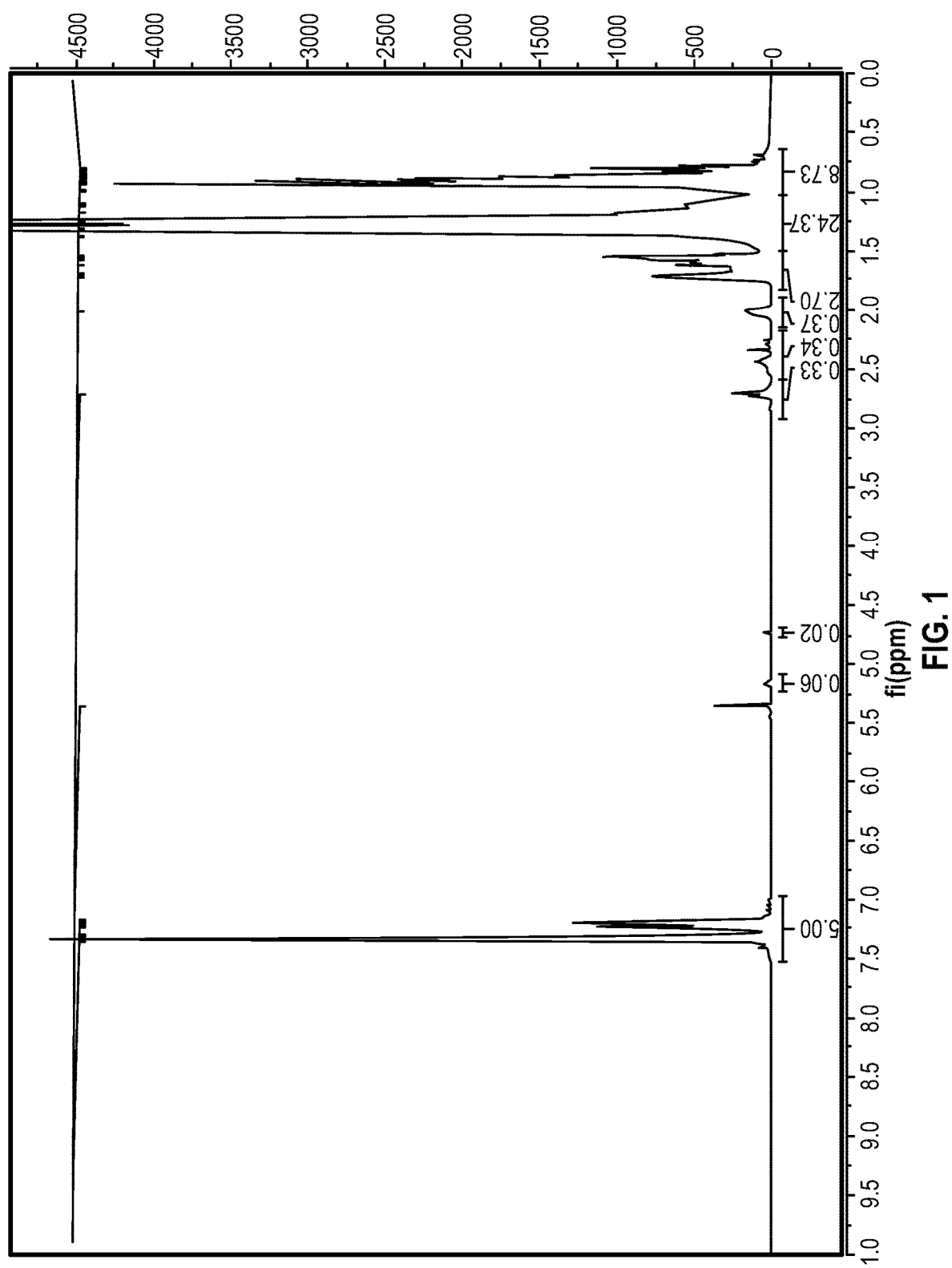
FIG. 1 shows a $^1$H NMR spectrum of the product of Example 1 in deuterated chloroform.

The present disclosure generally relates to amphiphilic compounds and, more specifically, to surfactants formed from vinylidene olefins and methods for production thereof.

As discussed above, most surfactants in common commercial use are based upon a relatively limited number of chemical structural classes. The various structural classes, as well as specific members or homologues within each structural class, may exhibit a range of surfactant properties, which may be chosen for suitability or compatibility with a given application. Some existing and emerging applications may have application-specific needs that are not adequately met by presently available surfactants. For example, certain conventional surfactants may not provide sufficient surface modification effects and/or adequate performance at decreased temperatures.

The present disclosure describes various classes of amphiphilic compounds that are reaction products of vinylidene olefins and that may exhibit surfactant properties Amphiphilic compounds of the present disclosure feature a hydrophobic portion formed, at least in part, from a vinylidene olefin, and a hydrophilic portion comprising a polar head group appended (bonded) directly or indirectly to the hydrophobic portion. Surfactants formed from vinylidene olefins are structurally distinct from most typical surfactants due to the presence of branching in the former. Branching may affect many surfactant properties such as packing factor, which is the ratio of the volume of the hydrophobic portion to an interfacial area occupied by the hydrophilic portion and the length of the hydrophobic portion. The surface activity of an amphiphilic compound may also be affected by branching within the hydrophobic portion.

Vinylidene olefins are often obtained synthetically as a mixture of olefins, possibly also including paraffinic compounds. The chain lengths of the vinylidene olefins may vary within a given olefin mixture, or optionally, the vinylidene olefins may be all of the same chain length. Additionally, some vinylidene olefins may contain branches, particularly methyl or ethyl branches, while some may have no branching. The position of the vinylidene group may vary as well.

Advantageously, vinylidene olefins may undergo a wide variety of reactions to form branched reaction products that may have surfactant properties. The double bond is consumed (becomes saturated) when forming the reaction products, thereby affording a hydrophobic portion derived, at least in part, from the vinylidene olefin and a hydrophilic portion featuring a polar head group bound directly or indirectly to the hydrophobic portion. Depending on particular application needs, various hydrophilic moieties may be introduced according to the disclosure herein, each retaining a branched structure that arises from the vinylidene olefin. Illustrative amphiphilic compounds that may be produced from vinylidene olefins according to the disclosure herein include surfactants comprising alkylbenzene sulfonates, primary alcohols, primary alcohol sulfates, primary alcohol alkoxylates, primary alcohol alkoxylate sulfonates, carboxylates, carboxylic acid esters, methyl ester sulfonates, and amine oxides, among others. In non-limiting examples, reactions such as, for example, hydroformylation, hydroboration, oxidation, epoxidation, and hydroxysulfonation of the vinylidene olefins may be employed to produce such amphiphilic compounds. Further description of the reactions that vinylidene olefins may undergo to produce the amphiphilic compounds of the present disclosure is provided below.

Unless otherwise indicated, room temperature is 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated is hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbons or hydrocarbyl groups may be one or more of linear, branched, cyclic, acyclic, saturated, unsaturated, aliphatic, or aromatic.

The terms "saturated" or "saturated hydrocarbon" refer to a hydrocarbon or hydrocarbyl group in which all carbon atoms are bonded to four other atoms or bonded to three other atoms with one unfilled valence position thereon.

The terms "unsaturated" or "unsaturated hydrocarbon" refer to a hydrocarbon or hydrocarbyl group in which one or more carbon atoms are bonded to less than four other atoms, optionally with one unfilled valence position on the one or more carbon atoms.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The term "alkyl" refers to a hydrocarbyl group having no unsaturated carbon-carbon bonds, and which may be optionally substituted. The term "alkylene" refers to an alkyl group having at least two open valence positions.

The term "alkenyl" refers to a hydrocarbyl group having a carbon-carbon double bond, and which may be optionally substituted. The terms "alkene" and "olefin" may be used synonymously herein. Similarly, the terms "alkenic" and "olefinic" may be used synonymously herein. Unless otherwise noted, all possible geometric and positional isomers are encompassed by these terms.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms.

Examples of saturated hydrocarbyl groups include, but are not limited to, methyl, ethyl, n-propyl, isopropyl, n-butyl, isobutyl, sec-butyl, tert-butyl, pentyl, isopentyl, hexyl, octyl, cyclopropyl, cyclobutyl, cyclopentyl, cyclohexyl, cyclooctyl, and the like, including their substituted analogues. Examples of unsaturated hydrocarbyl groups include, but are not limited to, ethenyl, propenyl, allyl, butadienyl, cyclopropenyl, cyclobutenyl, cyclopentenyl, cyclohexenyl, cyclooctenyl and the like, including their substituted analogues.

Examples of aromatic hydrocarbyl groups include, but are not limited to, phenyl, tolyl, xylyl, naphthyl, and the like, including all possible isomeric forms thereof. Polynuclear aromatic hydrocarbyl groups may include, but are not limited to, naphthalene, anthracene, indane, and indene.

The terms "oligomer(s)" and "oligomeric product" refer to a molecule having a predetermined number of repeating monomer units, where the number of repeating monomer units is relatively small and specifiable. Illustrative oligomers include dimers, trimers, tetramers, higher oligomers, and mixtures thereof. The term "oligomerization process" refers to any process of catalytically joining monomer units together to form an oligomer or oligomers. The term "oligomerization conditions" refers to any and all variations of equipment, reaction conditions (e.g., temperatures, pressures, and/or flow rates), materials, and reactor configurations that are suitable to conduct an oligomerization process.

The terms "linear" and "linear hydrocarbon" refer to a hydrocarbon or hydrocarbyl group having a continuous carbon chain without side chain branching, in which the continuous carbon chain may be optionally substituted with heteroatoms or heteroatom groups.

The terms "branch," "branched" and "branched hydrocarbon" refer to a hydrocarbon or hydrocarbyl group having a linear main carbon chain in which a hydrocarbyl side chain extends from the linear main carbon chain. Optional heteroatom substitution may be present in the linear main carbon chain or in the hydrocarbyl side chain.

The term "amphiphilic compound" refers to a compound having both a hydrophobic portion and a hydrophilic portion featuring a polar head group. The terms "polar head group" and "hydrophilic moiety" may be synonymously herein.

The term "ring atoms" refers to a plurality of atoms joined together in a loop to form a closed ring structure. Additional functional groups, rings, and/or chains may extend from is one or more of the ring atoms, with atoms in the additional functional groups, rings, and/or chains not being included in the count of ring atoms.

The term "ethoxylate" refers to the moiety —$(CH_2CH_2O)_a$—, wherein a is an integer ranging from 1 to 60, or 2 to 10.

The term "alkoxylate" refers to the moiety —$[(CH_2)_bO]_a$, wherein a is an integer ranging from 1 to 60, or 2 to 10, and b is an integer ranging from 2 to 10. The term alkoxylate refers to moieties such as ethoxylate (b=2), propoxylate (b=3), and ethoxylate/propoxylate mixtures.

The term "vinylidene" refers to an olefin moiety bearing two hydrogen atoms upon C-1 and two hydrocarbyl groups upon C-2 of the olefin moiety.

The term "trisubstituted" refers to an olefin moiety bearing two hydrocarbyl groups upon a first carbon atom of the olefin moiety and one hydrocarbyl group and one hydrogen atom upon a second carbon atom of the olefin moiety, wherein the olefin moiety is non-terminal.

The acronym "CMC" refers to critical micelle concentration given in wt %, where surface tension becomes independent of the surfactant concentration.

The acronym "ST" refers to surface tension, typically given in millinewtons (mN) per meter.

The term "wetting" refers to the ability of a liquid to maintain contact with a surface, typically measured in seconds.

The term "Krafft point" refers to the minimum temperature where micelles are formed, typically given in ° C.

Vinylidene Olefins

Reaction 1 below illustrates the general structure for a pair of linear alpha olefins (LAOs) and their subsequent dimerization to form an LAO dimer comprising a vinylidene group (i.e., a vinylidene olefin). For Reaction 1, R is an alkyl group having from 2 to 12 carbon atoms. The R groups in each LAO may be of the same length, or they may be of differing lengths. Optional methyl and/or ethyl branching may be present within the R groups. Alpha olefins having one methyl or ethyl branch per R group will also be considered to constitute linear alpha olefins for purposes of the present disclosure. Carbon atoms within the branches are not included in the total carbon count of the LAOs employed herein. As such, suitable vinylidene olefins may contain from 6 to 28 carbon atoms, not including any methyl or ethyl branches in the R groups.

Reaction 1

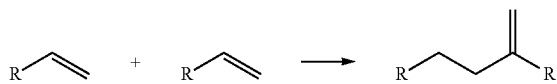

The corresponding disubstituted or trisubstituted olefin dimers may form as a side product during dimerization depending on the catalyst used. Formation of trisubstituted olefin dimers is shown in Reaction 2 below, wherein indeterminate olefin geometry is indicated by a wavy bond. The R groups are defined in the same manner as for Reaction 1, and the chain lengths of the LAOs undergoing dimerization may be the same or different. Again, optional branching may be present in the R groups.

Reaction 2

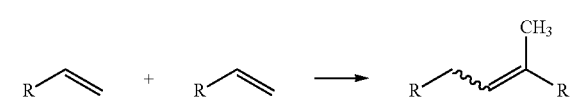

The corresponding trisubstituted olefin dimers may be removed from the vinylidene olefins prior to introduction of a polar head group thereto, according to some embodiments of the present disclosure. Alternately, trisubstituted olefin dimers may undergo functionalization to form a reaction product in combination with vinylidene olefins in some process configurations disclosed herein.

The LAO dimer resulting from Reaction 1 (LAO dimer comprising a vinylidene group) may be alternately characterized below as Structure 1, where $R^1$ is an alkyl group having from 2 to 12 carbon atoms and $R^2$ is an alkyl group having from 4 to 10 carbon atoms. The carbon count range for $R^1$ and $R^2$ differs in this case due to the manner in which the structure is defined (two carbon atoms from one of the LAOs are incorporated in the vinylidene group).

Structure 1

The reaction to form LAO dimers comprising a vinylidene group or a mixture of such LAO dimers in combination with a trisubstituted LAO dimer may be promoted by various metallocene catalyst systems. Catalyst systems suitable for oligomerizing LAOs into LAO dimers, particularly vinylidene or trisubstituted LAO dimers, may comprise a metallocene catalyst system, for example a bis(cyclopentadienyl)zirconium(IV) dichloride ($Cp_2ZrCl_2$), in combination with a suitable activator. Other non-limiting examples of metallocene catalysts that may be suitable to form LAO dimers comprising a vinylidene group include, for example, bis-(n-propylcyclopentadienyl) zirconium(IV) dichloride, bis(1-butyl-3-methylcyclopentadienyl) zirconium dichloride, Schwartz's reagent (zirconocene chloride hydride), or rac-dimethylsilyl-bis-(tetrahydroindenyl) zirconium dimethyl, each in combination with a suitable activator such as an alumoxane (e.g., methylalumoxane-MAO) or a non-coordinating anion activator. Still other suitable metallocene catalysts that may be used for synthesizing LAO dimers comprising a vinylidene group and/or trisubstituted LAO dimers may be found in commonly owned U.S. Patent Application Publication 2018/0282359, which is incorporated herein by reference in its entirety.

A non-coordinating anion (NCA) is defined to mean an anion either that does not coordinate to a transition metal center or that does coordinate to a transition metal center, but only weakly. The term NCA is defined to include multicomponent NCA-containing activators, such as N,N-dimethylanilinium tetrakis(pentafluorophenyl)borate and N,N-dimethylanilinium tetrakis(heptafluoronaphthyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. Typically, NCAs coordinate weakly enough that a neutral Lewis base, such as an olefin can displace it from the metal center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. The term non-coordinating anion includes neutral activators, ionic activators, and Lewis acid activators.

Particularly suitable NCAs may include, for example, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, triphenylcarbenium tetra(perfluorophenyl) borate, or any combination thereof.

Vinylidene Olefin Alkylbenzene Sulfonate Reaction Products

Vinylidene olefins may be used to form reaction products comprising alkylbenzene sulfonates and/or isomeric mixtures thereof, represented by Structures 2 and 2' below, among others, in which the variables are defined as above. In various embodiments, the amphiphilic compounds comprise an alkylation product of benzene or a substituted benzene and a vinylidene olefin, in which a polar head group comprising a sulfonate group is bound to the aromatic ring. As an initial step, one or more vinylidene olefins may be reacted with benzene or a substituted variant thereof in the presence of an acid catalyst to produce an alkylbenzene, in which one carbon of the olefin moiety has reacted electrophilically with the aromatic ring. Rearrangement of the carbocation formed from the vinylidene olefin during acid catalysis may favor alkylation at the more substituted carbon of the vinylidene olefin (Structure 2'). Depending on the catalyst used, alkylation at the terminal carbon atom may occur in some cases (Structure 2). Alternately, alkylation may occur at a carbon atom even more remote from the vinylidene olefin (e.g., through further carbocation rearrangement). The resulting alkylbenzene may then be contacted with a sulfur trioxide composition to form an alkylbenzene sulfonic acid, which may be subsequently neutralized with a base to produce an alkylbenzene sulfonate. The attachment site of the sulfonate substituent on the aromatic ring may vary among product isomers.

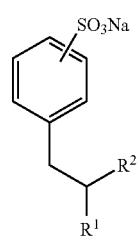

Structure 2

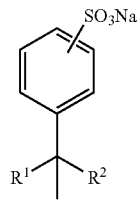

Structure 2'

To form products having Structures 2 and/or 2', benzene or a substituted variant thereof may be reacted with one or more vinylidene olefins in the presence of an acid catalyst to produce a reaction product comprising an alkylbenzene, as shown in Reaction 3 below. It will be understood that alternate isomers may be produced similarly. Illustrative acid catalysts may include, but are not limited to, HF, $AlCl_3$, solid acid catalysts such as ones based on MCM-49, MCM-22, MCM-41, UZM-8, USY, Mordenite, ZSM-12, $SO_4$-doped silica, and clay. Catalyst choice may influence the predominant product isomer formed. For example, MCM-49 may favors attachment at the terminal carbon atom, while USY may lead to alkylation at a non-terminal carbon atom (e.g., C-2). Reaction conditions are known in the art, and may vary based upon the catalyst used (e.g., temperatures from 10° C. to over 500° C., as specified in U.S. Pat. Nos. 4,954,325 and 5,334,795, which are incorporated herein by reference).

Reaction 3

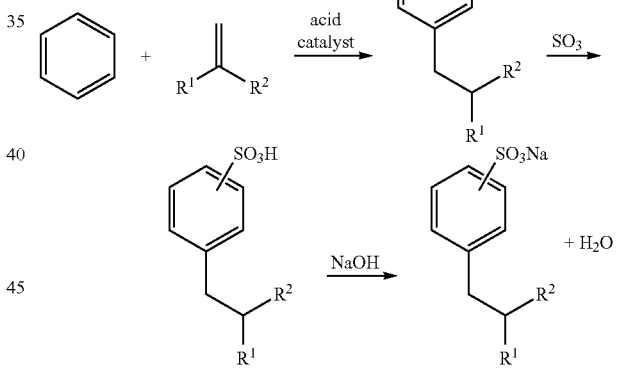

Unreacted benzene and vinylidene olefin(s), if present, may be removed by distillation before moving to subsequent steps in the production of amphiphilic compounds. Amphiphilic compounds may be produced via sulfonation of the alkylbenzene by reacting a sulfur trioxide composition with the aromatic ring to form alkylbenzene sulfonic acids. For example, sulfonation may be accomplished by reacting the alkylbenzene with $SO_3$ under falling film reactor conditions, or by reacting the alkylbenzene with oleum. The next step in the production of sulfonated amphiphilic compounds is neutralization of the resulting sulfonic acid with a base, such as, by way of non-limiting example, NaOH or KOH, to produce the sodium or potassium salt of the alkylbenzene sulfonate, which may exhibit surfactant properties.

Primary Alcohol Reaction Products

In some embodiments, vinylidene olefins may be reacted to form amphiphilic compounds that are long-chain alcohols having a primary alcohol functionality as the hydrophilic moiety, as shown in Structures 3, 3', 3" and 3'" below, in which the variables are defined as above, with the exception that $R^{1'}$ is an alkyl group having from 1 to 11 carbon atoms and $R^{2'}$ is an alkyl group having from 3 to 9 carbon atoms. Variable x in Structure 3 may be 0 or 1 depending upon how the primary alcohol is formed from the vinylidene olefin. As shown below, reaction products formed by a hydroformylation route have an additional carbon atom compared to the vinylidene olefin from which they were produced (x=1), and reaction products formed by a hydroboration route have the same number of carbon atoms as the vinylidene olefin from which they were produced (x=0). Hydroformylation may also occur with double bond migration, as shown in Structures 3' and 3" below. Structure 3 is a γ-branched long-chain alcohol, and Structures 3', 3" and 3'" are β-branched long alcohols.

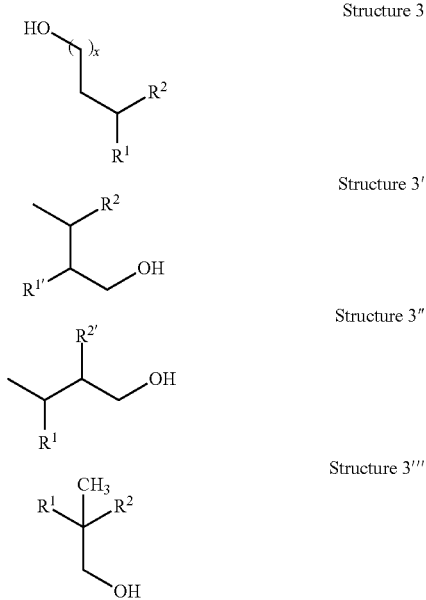

Structure 3

Structure 3'

Structure 3"

Structure 3'"

With reference to Reaction 4 below, vinylidene olefins may be hydroformylated in the presence of a catalyst to form an aldehyde using synthesis gas. Hydroformylation adds an additional carbon atom (as an aldehyde group) to the backbone of the vinylidene olefin and consumes the olefin moiety. Reaction 4 shows the formation of a γ-branched alcohol having Structure 3, but it is to be appreciated that β-branched alcohols having Structures 3', 3" and 3'" may be formed similarly. Synthesis gas or "syngas," a mixture of carbon monoxide and hydrogen, may be obtained through the use of partial oxidation technology, steam reforming, or a combination thereof that is often referred to as autothermal reforming. Suitable catalysts for the hydroformylation reaction of a vinylidene olefin may be a metal catalyst, typically a homogeneous metal carbonyl complex such as of a carbon monoxide complex of a transition metal of Group VIII of the Periodic Table. Of the Group VIII metals, cobalt and rhodium are best known for their hydroformylation activity, but others may include palladium, iridium, ruthenium and platinum. By way of nonlimiting example, suitable catalysts may include $HRh(CO)(PR_3)_3$, $HRh(CO)_2(PR_3)$, $HRh(CO)[P(OR)_3]_3$, $Rh(CH_3COCH_2COCH_3)(CO)_2$, $Rh_6(CO)_{16}$, [Rh(norbornadiene)$(PPh_3)_2$]$^+$ [PF$_6$]$^-$, [Rh(C)$_3$(PPh$_3$)$_2$]$^+$ [BPh$_4$]$^-$, $RhCl(CO)(PEt_3)_2$, [RhCl(cyclooctadiene)]$_2$, [Rh(CO)$_3$(PR$_3$)$_2$]$^+$ BPh$_4^-$, [Rh(CO)$_3$(PR$_3$)$_2$]$^+$ PF$_6^-$, HCo(CO)$_4$, Ru$_3$(CO)$_{12}$, [RuH(CO)(acetonitrile)$_2$(PPh$_3$)$_3$]$^+$ [BF$_4$]$^-$, PtCl$_2$(cyclooctadiene), [Ir(CO)$_3$ (PPh$_3$)]+[PF$_6$]$^-$, or [HPt(PEt$_3$)$_3$]$^+$ [PF$_6$]$^-$. Other suitable catalysts may include, for example, HCo(CO)$_4$, Co$_2$(CO)$_8$, HCo(CO)$_3$(POR)$_3$ (R=alkyl or aryl), HCo(CO)$_3$(PR$_3$) (R=alkyl or aryl), and Co(II)X$_2$ (X=anionic ligand, such as carboxylate, sulfate, halide, alkoxide, amide, etc.). Inorganic salts and catalyst precursors, such as RH$_2$O$_3$, Pd(NO$_3$)$_2$ and Rh(NO$_3$)$_3$, may be used, and halides such as, for example, RhCl$_3$·3H$_2$O (R=alkyl or aryl). In exemplary embodiments, a nickel catalyst in the presence of dimethylamine may be used. Hydroformylation may be carried out at temperatures from −20° C. to 250° C., or from 25° C. to 200° C., or from 30° C. to 150° C., or from 0° C. to 150° C., or from 0° C. to 120° C., or from 0° C. to 90° C., or from 0° C. to 50° C., or less than 85° C. Syngas pressures may range from 400 psig to 5000 psig, and the ratio of H$_2$:CO in the syngas may range from 0.3 to 0.7.

Reaction 4

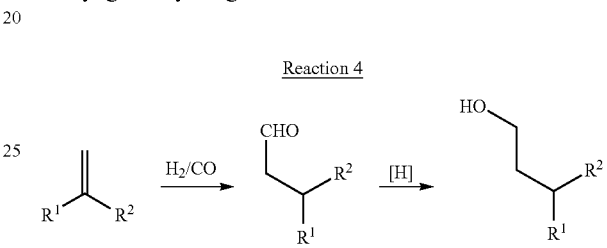

After hydroformylation, the resulting aldehyde may be hydrogenated or similarly reduced to form an alcohol. In this overall process, the vinylidene olefin is converted to a primary alcohol having one additional carbon atom. The alcohol may be γ-branched (Structure 3, x=1) or β-branched (Structures 3', 3" and 3'"). U.S. Pat. No. 5,674,950, which is incorporated herein by reference in its entirety, describes the hydroformylation process conditions in further detail.

Primary alcohol reaction products may also be produced from vinylidene olefins via hydroboration, which results in the formation of a hydroborated intermediate having a carbon-boron bond, as shown in Reaction 5 below. Hydroboration may be accomplished by contacting the vinylidene olefin with a boron hydride (e.g., B$_2$H$_6$) or a borane complex in the presence of a hydroboration catalyst, metal complex, or oxidizing agent to convert the carbon-boron bond into a primary alcohol. Hydroboration reaction temperatures may range from −50° C. to 200° C. The hydroborated intermediate may subsequently be reacted with a base and hydrogen peroxide to form a primary alcohol reaction product having the same number of carbon atoms as the vinylidene olefin from which it was produced (Structure 3, x=0).

Reaction 5

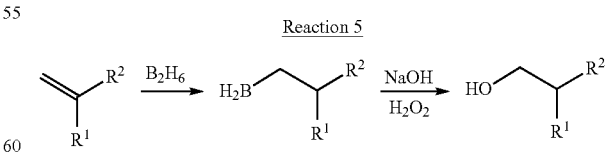

Diol Reaction Products

In some embodiments, vinylidene olefins may be reacted to form amphiphilic compounds having a glycol as the hydrophilic moiety as shown in Structure 4 below, in which the variables are defined as above. The glycol reaction products having Structure 4 are of the same carbon count as the vinylidene olefins from which they are produced.

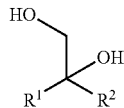

Structure 4

Vinylidene olefins may be oxidized to form glycol reaction products having Structure 4. Glycol formation may occur catalytically or stoichiometrically through reaction of the vinylidene olefins with a reagent such as, for example, $KMnO_4$, sodium periodate, or osmium tetroxide. Alternately, glycol reaction products may be formed via an epoxide intermediate, as shown in Reaction 6 below. Suitable oxidants for epoxidizing vinylidene olefins may include, for example, peracetic acid, m-chloroperoxybenzoic acid (MCPBA), dimethyldioxirane, and similar oxidants. The epoxide ring may then be opened with an aqueous acid to form a glycol, as shown in Reaction 6. Other nucleophiles may also open the is epoxide to form other amphiphilic compounds.

Reaction 6

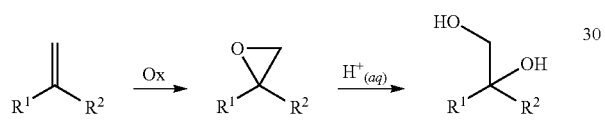

Vinylidene Olefin Alcohol Sulfate Reaction Products

In some embodiments, alcohols derived from vinylidene olefins may be derivatized to introduce a sodium salt of a sulfate group as the hydrophilic moiety, as shown in Structure 5, in which the variables are defined as above. It is to be appreciated that Structure 5 is illustrative of the alcohol sulfate reaction products that may be produced from primary alcohols prepared by hydroformylation or hydroboration according to the disclosure herein. For example, alcohol sulfate reaction products formed from β-branched alcohols may also be formed according to the disclosure herein, as shown in Structures 5', 5" and 5'''. Mono- or bis-sulfate reaction products of glycols also reside within the scope of the disclosure herein.

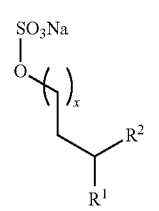

Structure 5

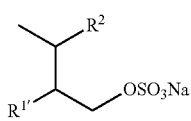

Structure 5'

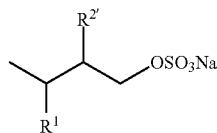

Structure 5"

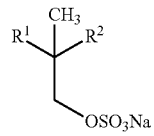

Structure 5'''

To form alcohol sulfates derived from vinylidene olefins, a primary alcohol may be reacted with a sulfur trioxide composition or chlorosulfuric acid to form the corresponding alcohol sulfate following neutralization, as shown in Reaction 7. Reaction 7 shows the formation of a γ-branched alcohol sulfate having Structure 5, but it is to be appreciated that β-branched alcohols having Structures 5', 5" and 5''' may be formed similarly. After sulfation, is the sulfated reaction product may be neutralized with a base (e.g., NaOH) to produce the corresponding sodium salt.

Reaction 7

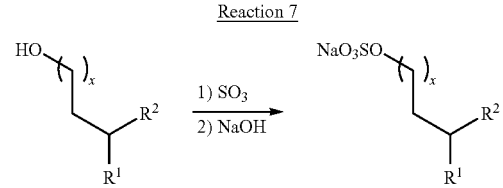

Vinylidene Olefin Alcohol Alkoxylate Reaction Products

In some embodiments, primary alcohols derived from vinylidene olefins may be derivatized to introduce an alkoxylate group (e.g., ethoxylate) as the hydrophilic moiety, as shown in Structure 6 below, wherein n is a positive integer and $R^3$ is H or a hydrocarbyl group, particularly a methyl group, and the other variables are defined as above. It is to be appreciated that a given sample may comprise a mixture of alkoxylate chain lengths, such that, on average, variable n has a non-integer value. A typical value for variable n when ethoxylating with ethylene oxide is 8 to 10 ($R^3$=H). The alkoxylates may be ethoxylate and/or propoxylate groups in particular embodiments of the present disclosure. It is to be appreciated that Structure 6 is illustrative of the alcohol alkoxylate reaction products that may be produced from γ-branched primary alcohols prepared by hydroformylation or hydroboration according to the disclosure herein. For example, alcohol alkoxylate reaction products formed from γ-branched alcohol sulfates may also be formed according to the disclosure herein, as shown in Structures 6', 6" and 6'''. Mono- or bis-alkoxylate reaction products of glycols also reside within the scope of the disclosure herein.

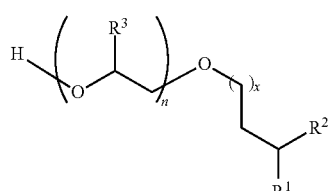

Structure 6

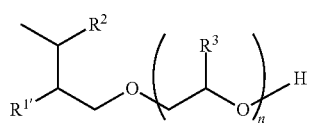

Structure 6'

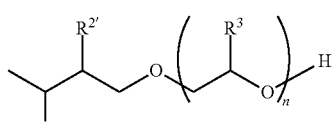

Structure 6"

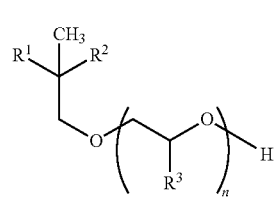

Structure 6'''

As shown in Reaction 8 below, a primary alcohol derived from a vinylidene olefin may subsequently undergo alkoxylation using ethylene oxide, propylene oxide, or any combination thereof to form the corresponding ethoxylate, propoxylate, or combination thereof. Reaction 8 shows the formation of a γ-branched alcohol alkoxylate having Structure 6, but it is to be appreciated that β-branched alcohol alkoxylates having Structures 6', 6" and 6''' may be formed similarly. The alcohol ethoxylate/propoxylate produced may be a homopolymer or a random or block copolymer of ethylene oxide and/or propylene oxide units attached to alcohol. It is to be appreciated that the reaction product formed from propylene oxide is not limited to the specific regioisomer shown.

Reaction 8

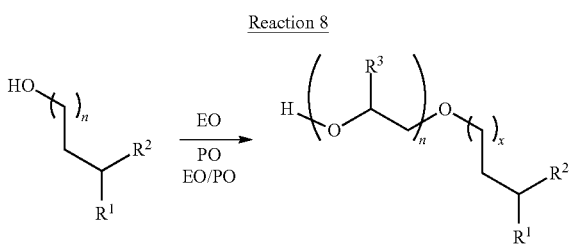

Vinylidene Olefin Alcohol Alkoxylate Sulfate Reaction Products

In some embodiments, a primary alcohol derived from a vinylidene olefin may be derivatized to introduce an alkoxylate group (e.g., ethoxylate) and a sulfate group as the hydrophilic moiety, as shown in Structure 7, in which the variables are defined as above. A typical value for x when ethoxylating with ethylene oxide is 8 to 10 ($R^3$=H). The alkoxylates may be ethoxylate and/or propoxylate groups in particular embodiments of the present disclosure. It is to be appreciated that Structure 7 is illustrative of the alcohol alkoxylate sulfate reaction products that may be produced from primary alcohols prepared by hydroformylation or hydroboration according to the disclosure herein. For example, alcohol alkoxylate sulfate reaction products formed from β-branched primary alcohols may also be formed according to the disclosure herein, as shown in Structures 7', 7" and 7'''. Mono- or bis-alkoxylate reaction products of glycols also reside within the scope of the disclosure herein.

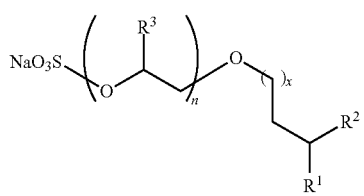

Structure 7

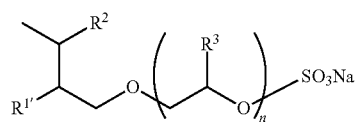

Structure 7'

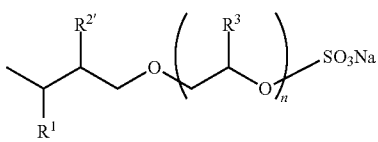

Structure 7"

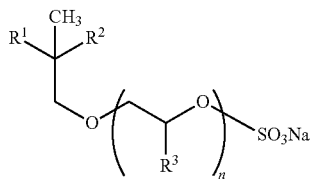

Structure 7'''

After alkoxylation of the primary alcohol derived from the vinylidene olefin, the terminal alcohol of the alkoxylate may be further converted into a sulfate salt by reacting the terminal alcohol with $SO_3$ or chlorosulfuric acid and then neutralizing the resulting sulfuric acid with a base, as shown in Reaction 9. Reaction 9 shows the formation of a γ-branched alcohol alkoxylate sulfate having Structure 7, but it is to be appreciated that β-branched alcohol alkoxylate sulfates having Structures 7', 7" and 7''' may be formed similarly.

Reaction 9

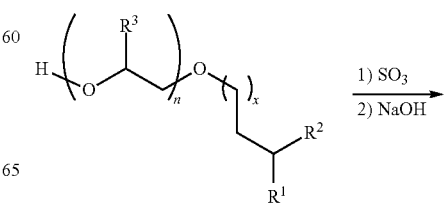

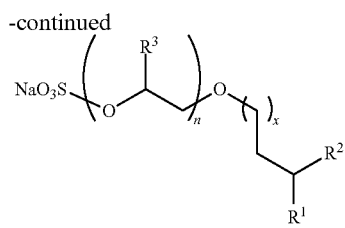

Vinylidene Olefin Carboxylate Reaction Products

In some embodiments, vinylidene olefins may be derivatized to amphiphilic compounds having a carboxylate as the hydrophilic moiety, as shown in Structures 8, 8', 8" and 8''' below, in which y is 0 or 1 and the other variables are defined as above. The carboxylate reaction products of Structure 8 are one carbon larger than the vinylidene olefin from which they are produced when formed from a hydroformylated intermediate (y=1) and have the same carbon count when prepared from a hydroborated intermediate (y=0).

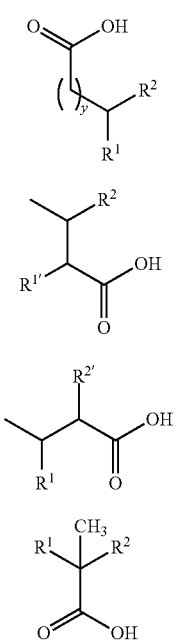

As described above, an intermediate aldehyde is produced during hydroformylation of vinylidene olefins. Instead of reducing the aldehyde to form a primary alcohol, as above, the aldehyde may alternately be oxidized to form a carboxylic acid variant of the vinylidene olefins. Oxidation may be carried out, for example, by contacting the intermediate aldehyde with oxygen in the presence of a multimetallic catalyst under oxidation conditions that are known in the art. Other standard oxidation conditions for converting an aldehyde into a carboxylic acid may also be used. In the net reaction, the vinylidene olefin is converted to a carboxylic acid having an additional carbon atom, as shown in Reaction 10. Reaction 10 shows is the formation of a γ-branched carboxylate having Structure 8, but it is to be appreciated that β-branched carboxylates having Structures 8', 8" and 8''' may be formed similarly. Reaction 10' shows the corresponding formation of a carboxylate formed via hydroboration of a vinylidine olefin. Following oxidation, the carboxylic acid may be neutralized with a base such as, for example, NaOH to form the sodium salt of the carboxylic acid. Other bases may also be suitable.

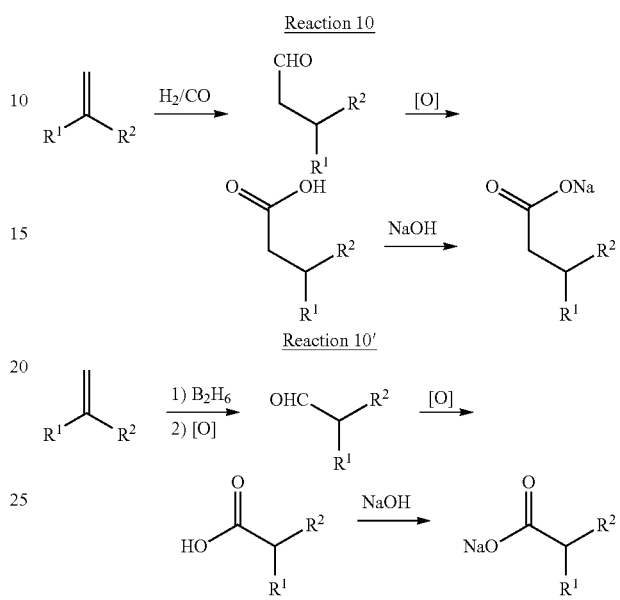

Vinylidene Olefin Carboxylic Acid Ester Reaction Products

Carboxylic acids derived from vinylidene olefins (Structures 8, 8', 8" and 8''') may be converted to an ester by esterification methods known in the art to form, for example, glyceryl, polyglyceryl, propylene glycol, and/or sorbitol esters, as shown in Reaction 11 below, in which the variables are defined as above. In Reaction 11, $R^4$ represents a hydrocarbyl group, including those comprising a glyceryl, polyglyceryl, propylene glycolate, or sorbitol ester moiety. Although Reaction 11 has shown esterification to take place using a carboxylic acid produced via a hydroformylated intermediate, it is to be appreciated that similar chemistry may be conducted using a carboxylic acid having an alternative chain length, if desired. Similarly, Reaction 11 shows the reaction of a γ-branched carboxylate having Structure 8, but it is to be appreciated that β-branched carboxylates having Structures 8', 8" and 8''' may be reacted similarly.

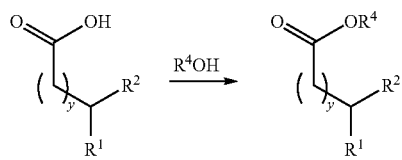

Vinylidene Olefin Methyl Ester Sulfonate Reaction Products

Additionally, carboxylic acid reaction products derived from a vinylidene olefin may be converted into the corresponding methyl ester, which may be subsequently sulfonated and neutralized, as shown in Reaction 12, in which the variables are defined as above.

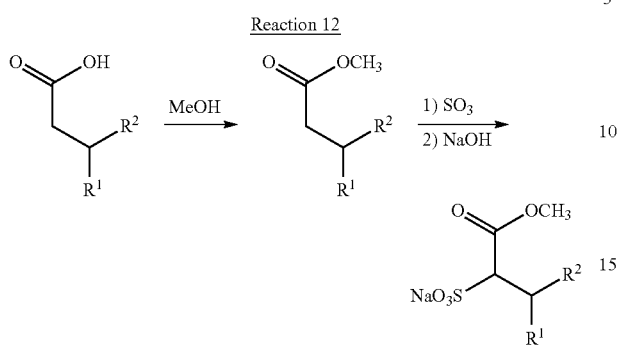

Although Reaction 12 has shown esterification and sulfonation to take place using a carboxylic acid produced via a hydroformylated intermediate, it is to be appreciated that other methyl ester sulfonate reaction products having related structures may be formed similarly, including those having β-branching.

Vinylidene Olefin Amine Oxide Reaction Products

Vinylidene olefins may be reacted to form amphiphilic compounds having an amine oxide as the polar head group, as shown in Structures 9, 9', 9" and 9'", in which the variables are defined as above.

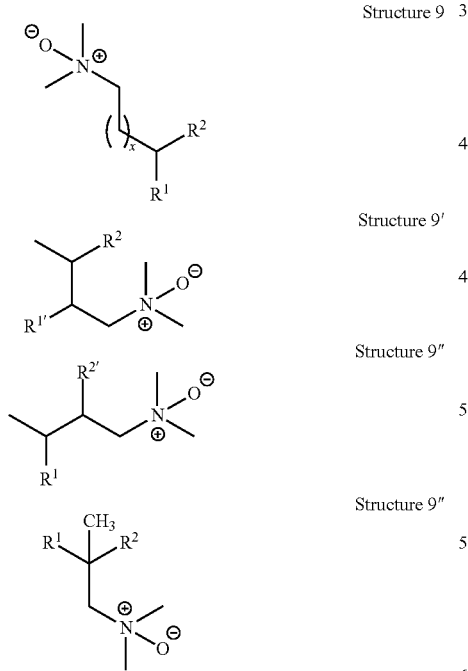

Depending on whether the amine oxide reaction product is prepared via a hydroformylated intermediate or a hydroborated intermediate, the backbone of the amine oxide reaction product may have the same number of carbon atoms or a different number of carbon atoms than the vinylidene olefin. Synthesis of the amine oxide reaction product corresponding to Structure 9 may take place according to Reaction 13 below, wherein the amine oxide reaction product is prepared from a hydroformylated intermediate and has one additional carbon atom compared to the vinylidene olefin from which it was produced. Reaction 13 shows the formation of a γ-branched amine oxide having Structure 9, but it is to be appreciated that β-branched amine oxides having Structures 9', 9" and 9'" may be formed similarly.

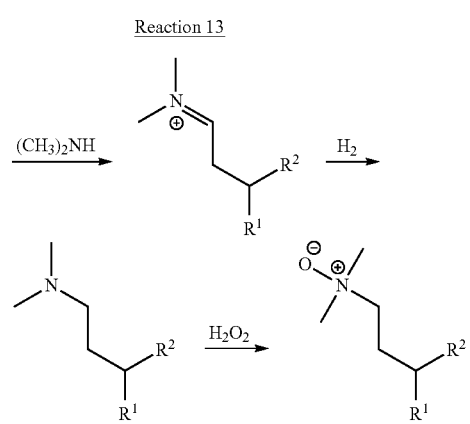

Synthesis of an amine oxide reaction product having the same number of carbon atoms as the vinylidene olefin from which it was produced is shown in Reaction 13' below.

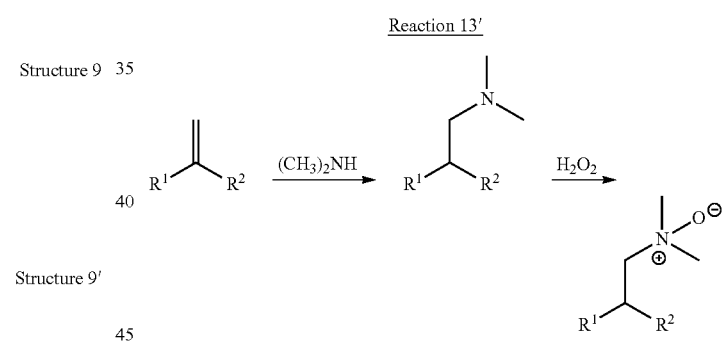

Surfactant Compositions

The above-disclosed reaction products derived from vinylidene olefins may be formulated in solid form or dispersed or dissolved in a fluid phase to form suitable surfactant compositions for use in particular applications. The fluid phase may comprise an aqueous fluid in some embodiments. The surfactant compositions may be a detergent formulation in particular instances.

Surfactant compositions of the present disclosure may comprise an aqueous fluid, and a vinylidene olefin reaction product that is present in the aqueous fluid at a concentration ranging from 10 wt % to 80 wt %.

Surfactant compositions of the present disclosure may comprise an aqueous fluid in which one or more vinylidene olefin reaction products described herein are dissolved or dispersed. Suitable aqueous fluids are not particularly limited and may be selected from deionized water, tap water, fresh water, surface water, ground water, brackish water, salt water, sea water, brine, or any combination thereof. Other aqueous fluid sources may also be suitable. The aqueous fluid may further comprise a water-miscible organic solvent such as one or more alcohols, for example, in some embodiments.

When dissolved in a suitable aqueous fluid, the reaction products disclosed herein may exhibit a range of surfactant properties. According to some embodiments, the reaction products may be present in the aqueous fluid above a critical micelle concentration.

Exemplary suitable applications of the surfactant compositions disclosed herein include, by way of non-limiting example, household laundry liquids, household laundry detergent capsules, household machine dishwash capsules, household hand dishwash liquids, and industrial/institutional laundry detergents.

For household laundry liquids, the total surfactant content may be 10 wt % to 50 wt % of the total laundry liquid. Other components may include, for example, enzymes, polymers, builders, complexing agents, and solvents in addition to water. The surfactants may comprise one or more reaction products disclosed herein, such as alkylbenzene sulfonates, alcohol ethoxylate sulfates, alcohol ethoxylates, amine oxides, and carboxylates. In addition to the reaction products disclosed herein, other conventional surfactants may also be present.

For household laundry detergent capsules, the total surfactant content may be from 40 wt % to 70 wt % of the household laundry detergent capsules. Other components may include, for example, enzymes, polymers, builders, complexing agents, and solvents in addition to water. The surfactants may comprise one or more reaction products disclosed herein, such as alkylbenzene sulfonates, alcohol ethoxylate sulfates, alcohol ethoxylates, amine oxides, and carboxylates. In addition to the reaction products disclosed herein, other conventional surfactants may also be present.

Household machine dishwash capsules may contain a total surfactant content from 10 wt % to 30 wt % of the capsules. The remaining components may comprise one or more of enzymes, polymers, builders, complexing agents, solvents, and fillers in addition to water. The surfactants may comprise one or more reaction products disclosed herein, such as alcohol ethoxylates and/or propoxylates. In addition to the reaction products disclosed herein, other conventional surfactants may also be present.

Household hand dishwash liquids may contain a total surfactant content from 10 wt % to 30 wt % of the liquid. The remaining components may comprise one or more of builders, polymers, complexing agents, fillers and solvents in addition to water. The surfactants may comprise one or more reaction products disclosed herein, such as alcohol ethoxylates and/or propoxylates, or amine oxides. In addition to the reaction products disclosed herein, other conventional surfactants may also be present.

For industrial applications such as industrial or institutional laundry detergent, total surfactant content may be from 10 wt % to 40 wt % by weight of the detergent. Other components may include alkalis, such as sodium hydroxide; inorganic salt, such as sodium metasilicate, pentasodium triphosphate, and polymeric material such as the sodium salt of polyacrylic acid; solvents; and enzymes. The surfactant system may be composed of one or more of alcohol ethoxylates, alcohol propoxylates, alcohol ethoxylate/propoxylates, alkylamine ethoxylate, alcohol alkoxylate sulfates, or alkylbenzene sulfonates, such as the reaction products disclosed herein. In addition to the reaction products disclosed herein, other conventional surfactants may also be present.

Embodiments disclosed herein include:

A. Compositions comprising one or more amphiphilic compounds. The compositions comprise: a reaction product of one or more vinylidene olefins, the reaction product comprising a hydrophobic portion and a hydrophilic portion comprising a polar head group bonded to the hydrophobic portion; wherein the one or more vinylidene olefins comprise a vinylidene group that undergoes a reaction to become saturated and to bond the polar head group to the hydrophobic portion.

B. Detergent formulations. The detergent formulations comprise: an aqueous fluid; and a surfactant comprising a reaction product of one or more vinylidene olefins, the reaction product comprising a hydrophobic portion and a hydrophilic portion comprising a polar head group bonded to the hydrophobic portion; wherein the one or more vinylidene olefins comprise a vinylidene group that undergoes a reaction to become saturated and to bond the polar head group to the hydrophobic portion; wherein the surfactant is present in the aqueous fluid at a concentration ranging from 10 wt % to 80 wt %.

Each of embodiments A and B may have one or more of the following additional elements in any combination:

Element 1: wherein the reaction product is an alkylation product of an aromatic ring, and the polar head group is a sulfonate group bound to the aromatic ring.

Element 2: wherein the reaction product is a hydroformylation reaction product in which an aldehyde group formed during hydroformylation is reduced to a primary alcohol or a derivative of a primary alcohol, the primary alcohol or the derivative of the primary alcohol comprising the polar head group.

Element 3: wherein the reaction product is a hydroboration reaction product comprising a primary alcohol or a derivative of a primary alcohol, the primary alcohol or the derivative of the primary alcohol comprising the polar head group.

Element 4: wherein the derivative of the primary alcohol is an alcohol sulfate.

Element 5: wherein the derivative of the primary alcohol is an alcohol alkoxylate.

Element 6: wherein the derivative of the primary alcohol is an alcohol alkoxylate sulfate.

Element 7: wherein the derivative of the primary alcohol is selected from the group consisting of an alcohol sulfate, an alcohol alkoxylate, an alcohol alkoxylate sulfate, and any combination thereof.

Element 8: wherein the reaction product is an oxidation product comprising a glycol or a derivative of a glycol, the glycol or the derivative of the glycol comprising the polar head group.

Element 9: wherein the derivative of the glycol is selected from the group consisting of a glycol mono-sulfate, a glycol bis-sulfate, a glycol mono-alkoxylate, a glycol bis-alkoxylate, and any combination thereof.

Element 10: wherein the reaction product is a hydroformylation reaction product in which an aldehyde group formed during hydroformylation is oxidized to a carboxylic acid or a derivative of a carboxylic acid, the carboxylic acid or the derivative of the carboxylic acid comprising the polar head group.

Element 11: wherein the derivative of the carboxylic acid is selected from the group consisting of a carboxylate salt, a carboxylic acid ester, a methyl ester sulfate, and any combination thereof.

By way of non-limiting example, exemplary combinations applicable to A and B include, but are not limited to, Element 2 in combination with one or more of Elements 4 to 7; Element 3 in combination with one or more of Elements 4 to 7; Element 8 in combination with Element 9; and Element 10 in combination with Element 11.

To facilitate a better understanding of the embodiments described herein, the following examples of various representative embodiments are given. In no way should the following examples be read to limit, or to define, the scope of the present disclosure.

EXAMPLES

Example 1: To produce an alkylbenzene sulfonate reaction product, 4.0 g of pre-dried MCM-49-based catalyst was placed in a catalyst basket of a Parr autoclave (the reactor). The catalyst was dried in the reactor for 1 hour at 160° C. under $N_2$ flow. Benzene (120 g) was subsequently introduced to the reactor at 150° C. and agitated from 400-500 rpm. The temperature was allowed to equilibrate for 30 min before 94.8 g of 2-hexyl-1-decene was introduced. The reactor pressure was maintained at 300 psig under $N_2$ flow and a consistent temperature of 150° C. The reaction was monitored by taking approximately 1 mL aliquots of offline sample via dip tube sample line and analyzing by gas chromatography (GC), both flame ionization detector (FID) GC and mass spectrometry (MS) GC. After 17.5 hours, the conversion of olefin was 95%.

Figure 2:
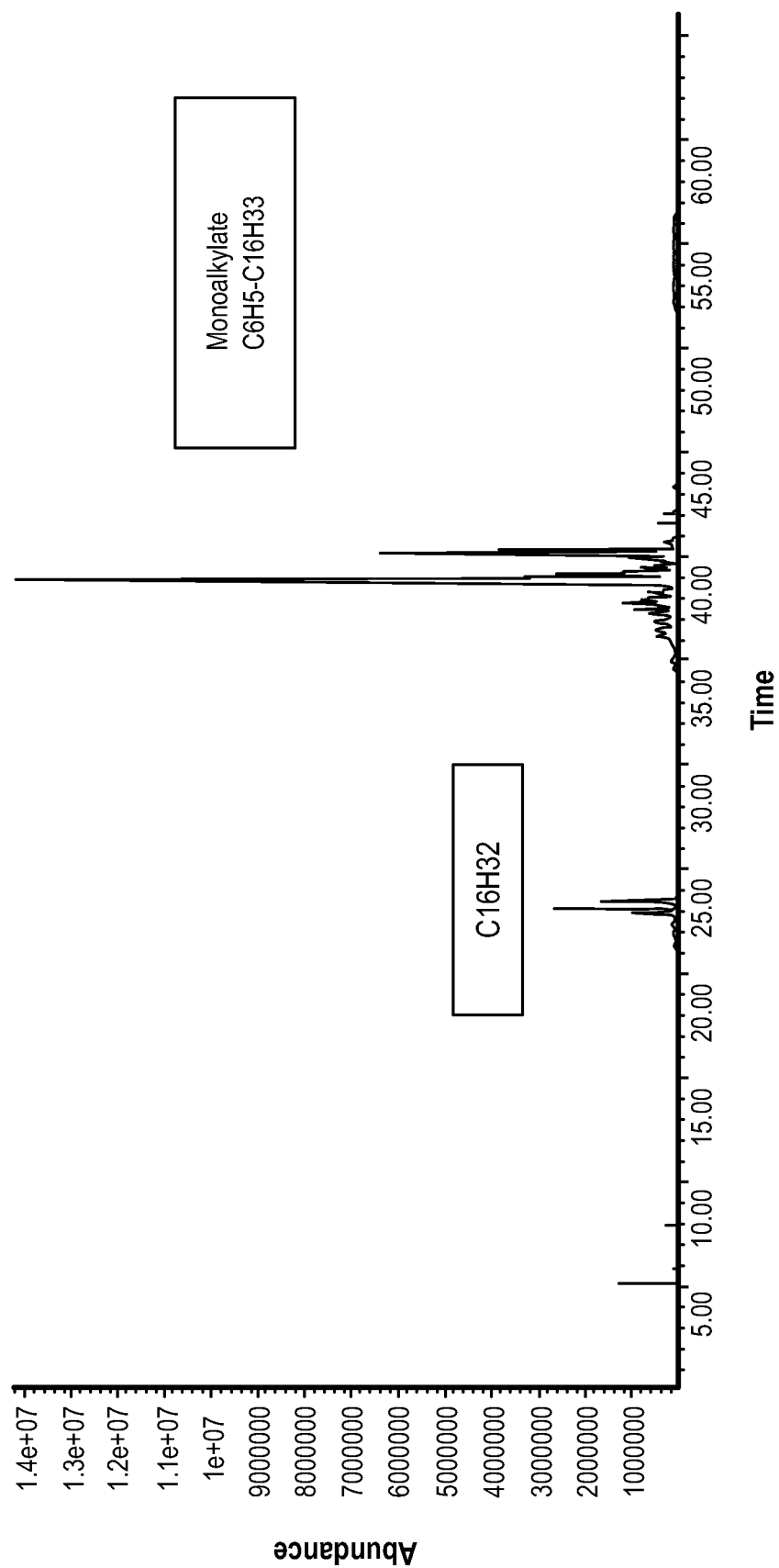
FIG. 2 shows a gas chromatography flame ionization desorption spectrum of the product of Example 1.
Figure 3:
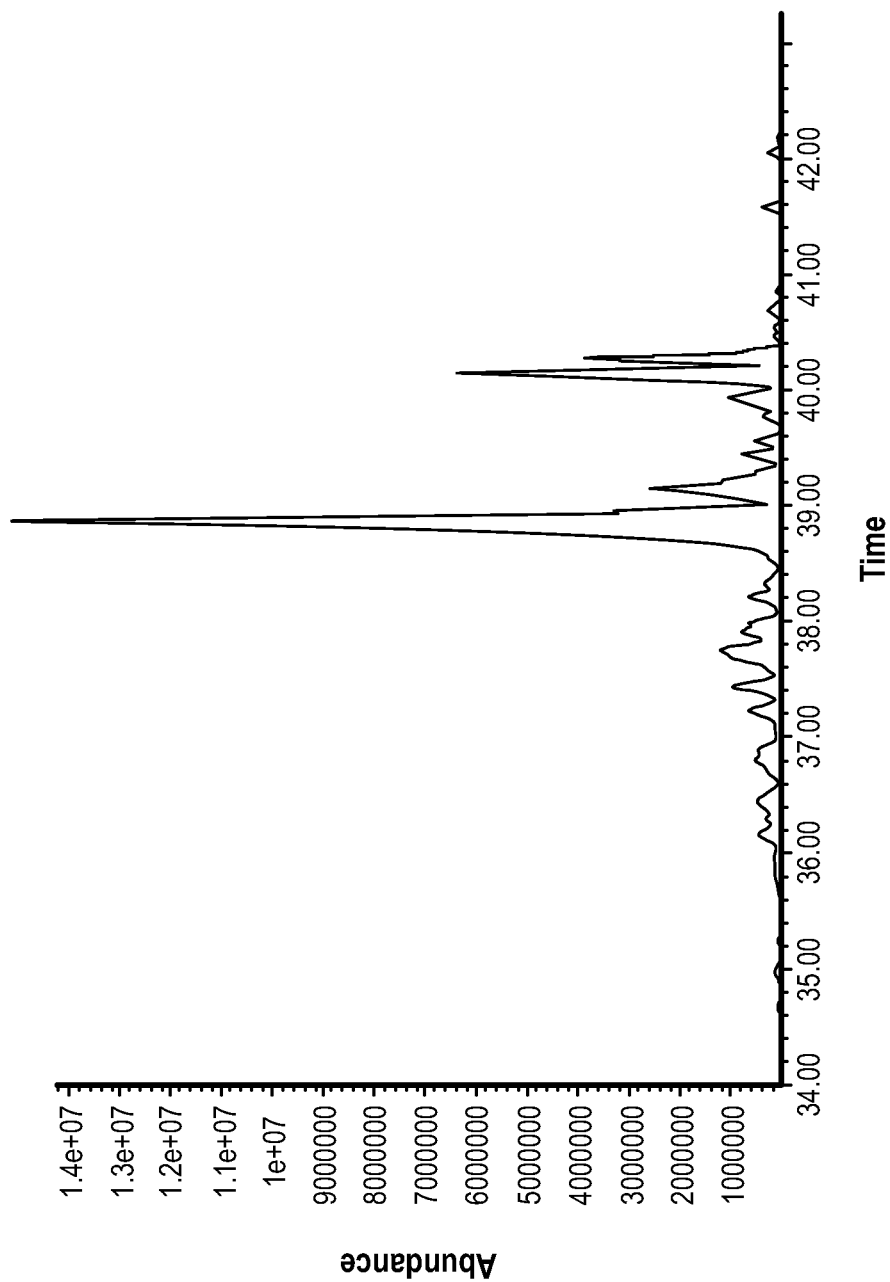
FIG. 3 shows a detailed view of the monoalkylated product region of FIG. 2.

Analysis of the product in deuterated chloroform via $^1$H NMR (FIG. 1) confirmed that the reaction product was predominately monoalkylated, with an insignificant amount of dialkylate/polyalkylate (<1%). The product was analyzed via GC-FID (FIGS. 2 and 3), and showed a strong signal between 38 and 41 minutes, indicating that monoalkylates predominated.

Figure 4:
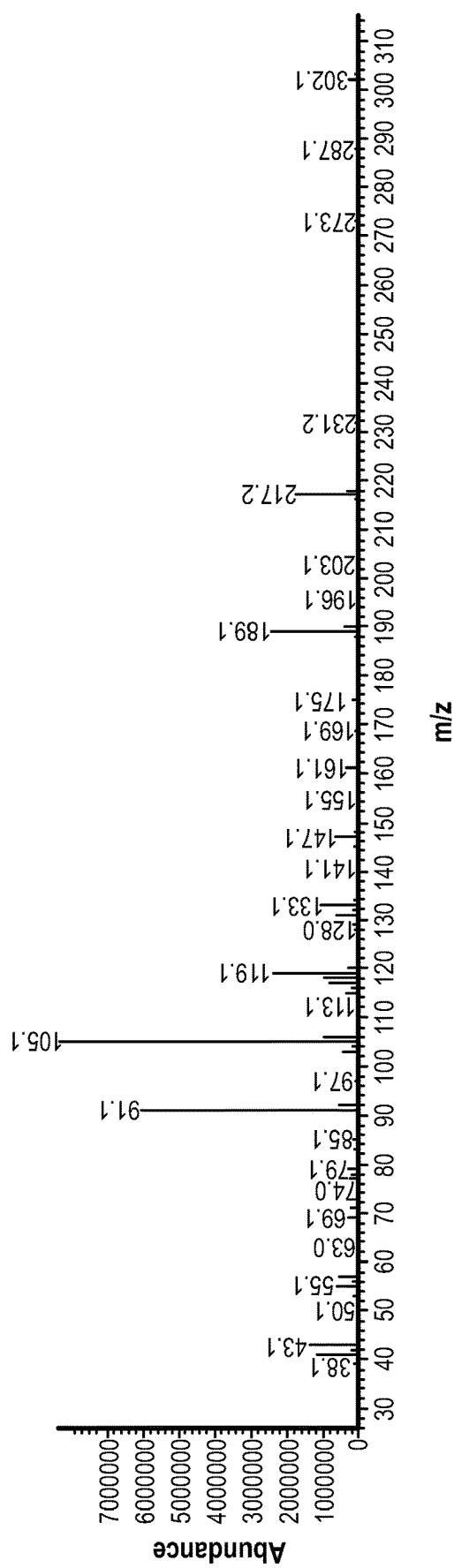
FIG. 4 shows a gas chromatography-mass spectrometry analysis of the product of Example 1.

After cooling, the reactor content was collected. Unreacted benzene and 2-hexyl-1-decene were removed under reduced pressure using a rotary evaporator. After rotary evaporation, 101.1 g of clear, colorless liquid was collected. In the final product analysis by gas chromatography-mass spectrometry (FIG. 4), the majority isomer within the alkylated product was (2-hexyldecyl)benzene. Remaining 2-hexyl-1-decene in the final product was less than 5%, as determined by gas chromatography-flame ionization detector.

The resulting $C_{16}$ alkylbenzene (52.1 g) was subsequently sulfonated by reaction with oleum (55.9 g). While stirring, oleum was slowly dripped into the flask at a temperature between 25-35° C., using an ice bath if necessary to hold the temperature steady. After addition of all of the oleum, the contents of the flask were maintained at 25-35° C. with stirring for 30 minutes. Sulfuric and sulfonic acid levels were monitored periodically and the flask was continually stirred until the sulfuric and sulfonic acid levels were unchanged at 1.09 me/g sulfonic, 35.53% sulfonic acid, and 51.46% sulfuric acid. Subsequently, 10% water was added to the reaction mixture and mixed for 30 minutes. The sample was poured into centrifuge tubes and placed in a 60° C. oven overnight. The sample was centrifuged to separate upper and lower layers. Samples (5 g) were carefully removed from the top layer, and analyzed for sulfuric and sulfonic acids. The remainder was centrifuged, and additional samples were taken. This procedure was repeated and sulfonic acid samples were accumulated (Table 1) until the sulfonic acid decreased in concentration.

TABLE 1

| Sample | $H_2SO_4$ [%] | Sulfonic acid [me/g] | Sulfonic acid [%] |
|---|---|---|---|
| 1 | 9.02 | 2.05 | 66.83 |
| 2 | 9.44 | 2.14 | 70.19 |
| 3 | 7.95 | 2.14 | 70.19 |
| 4 | 8.75 | 1.97 | 64.22 |
| 1-4 combined | 8.23 | 2.00 | 66.20 |

Performance tests were run by making a 1.00 wt % active sodium sulfonate, and then diluting to the desired concentration. The alkylbenzene sulfonate reaction product produced from 2-hexyl-1-decene was compared to a commercially available linear alkyl benzene sulfonate, NAACONOL® 90G (available from Stepan Company), a linear analog of slightly different chain length. Results are shown in Table 2 below.

TABLE 2

| | Example Product | Commercial Product |
|---|---|---|
| CMC [wt %] | 0.06 | 0.0156[3] |
| ST @ CMC [mN/m] | 29 | 34 |
| $C_{20}$ [wt %] | 0.0004 | 0.007 |
| Foaming 0.1% Initial [mm] | 134 | 170 |
| Foaming 0.1% 5 min [mm] | 123 | 132 |
| Wetting 0.1% [sec] | 43.1 | 4.3 |
| Ca tolerance [mg/g] | 36.4 | 58 |
| Krafft Point [° C.] | 55.0 | <2 |

Surfactant activities were measured using conditions specified in ASTM D3049. Critical micelle concentrations in water and 1% NaCl solution, surface tension values at the critical micelle concentration, and $C_{20}$ values were measured using conditions specified in ISO 4311. Foaming properties were measured using conditions specified in ASTM D1173-07. Wetting was measured using conditions specified in ASTM D2281. $C_{20}$ values represent the surfactant concentration needed to decrease the surface tension of the solvent by 20 mN/m.

Calcium tolerance was tested using the following procedure. A 0.1 wt % solution of the surfactant was prepared by dissolving 0.050 g of the surfactant in 50 mL of distilled water in a 200 mL Erlenmeyer flask. This solution was used as a blank to set a turbidity value of 0 on a LaMotte 2020 Turbidity Meter. A 1.00 wt % solution of calcium chloride was titrated into the surfactant solution in 0.20 mL increments using a 5 mL micro-buret. The solution was then mixed and the turbidity was read again after each calcium chloride aliquot addition. The haze reading was then plotted against the titer (volume of added calcium chloride solution). The amount of added calcium chloride solution needed to produce a haze reading of 50 was then determined. This reading represents the lowest perceptible haze. The titer volume and concentration and the sample concentration may then be used to determine the number of milligrams of calcium that may be tolerated per gram of sample before haziness occurs.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure.

What is claimed is:

1. A composition comprising:
   a reaction product of one or more vinylidene olefins, the reaction product comprising a hydrophobic portion and a hydrophilic portion comprising a polar head group bonded to the hydrophobic portion;
   wherein the one or more vinylidene olefins each comprise a vinylidene group that undergoes a reaction to become saturated and to produce at least part of the hydrophobic portion,
   wherein the reaction product is an oxidation product comprising a glycol or a derivative of a glycol, the glycol or the derivative of the glycol including the polar head group.

2. The composition of claim 1, wherein the derivative of the glycol is selected from the group consisting of a glycol mono-sulfate, a glycol bis-sulfate, a glycol mono-alkoxylate, a glycol bis-alkoxylate, and any combination thereof.

3. A detergent formulation comprising:
   an aqueous fluid; and
   a surfactant comprising a composition according to claim 1;
   wherein the surfactant is present in the aqueous fluid at a concentration ranging from 10 wt % to 80 wt %.

* * * * *